United States Patent
Smith et al.

(10) Patent No.: US 9,169,202 B2
(45) Date of Patent: Oct. 27, 2015

(54) SURFACE ACTIVE AGENTS DERIVED FROM BIODIESEL-BASED ALKYLATED AROMATIC COMPOUNDS

(75) Inventors: George A. Smith, The Woodlands, TX (US); Daniel R. Weaver, Spring, TX (US); Zheng Chai, Spring, TX (US)

(73) Assignee: HUNTSMAN PETROCHEMICAL LLC, The Woodlands, TX (US)

( * ) Notice: Subject to any disclaimer, the term of this patent is extended or adjusted under 35 U.S.C. 154(b) by 202 days.

(21) Appl. No.: 13/823,022

(22) PCT Filed: Sep. 19, 2011

(86) PCT No.: PCT/US2011/052085
§ 371 (c)(1),
(2), (4) Date: Mar. 20, 2013

(87) PCT Pub. No.: WO2012/050738
PCT Pub. Date: Apr. 19, 2012

(65) Prior Publication Data
US 2013/0172589 A1    Jul. 4, 2013

Related U.S. Application Data

(60) Provisional application No. 61/388,224, filed on Sep. 30, 2010.

(51) Int. Cl.
| | | |
|---|---|---|
| C07C 51/00 | (2006.01) | |
| C07C 309/58 | (2006.01) | |
| C08K 5/10 | (2006.01) | |
| C08K 5/42 | (2006.01) | |
| C07C 67/343 | (2006.01) | |
| C07C 69/612 | (2006.01) | |
| C07C 303/32 | (2006.01) | |

(52) U.S. Cl.
CPC ............ *C07C 309/58* (2013.01); *C07C 67/343* (2013.01); *C07C 69/612* (2013.01); *C07C 303/32* (2013.01); *C08K 5/10* (2013.01); *C08K 5/42* (2013.01)

(58) Field of Classification Search
CPC .. C07C 309/58; C07C 317/46; C07C 317/48; C07C 403/04; C07C 403/08
USPC ........................................... 554/95, 162, 220
See application file for complete search history.

(56) References Cited

U.S. PATENT DOCUMENTS

| | | | |
|---|---|---|---|
| 2,548,018 A | | 10/1948 | Hedrick |
| 2,845,448 A | * | 7/1958 | Taylor .............................. 558/52 |
| 3,429,136 A | * | 2/1969 | Mueller et al. .................. 62/114 |
| 4,310,471 A | * | 1/1982 | Oswald et al. .................. 558/56 |
| 6,802,897 B1 | | 10/2004 | Lackey et al. |
| 7,629,487 B2 | | 12/2009 | Smith et al. |
| 2007/0066504 A1 | * | 3/2007 | Hsu et al. ...................... 510/276 |

OTHER PUBLICATIONS

M. Franek, et al. "Antibody-based methods for surfactant screening", Fresenius' Journal of Analytical Chemistry, vol. 371, No. 4, Sep. 25, 2001, pp. 456-466.

* cited by examiner

*Primary Examiner* — Deborah D Carr
(74) *Attorney, Agent, or Firm* — Huntsman International LLC

(57) ABSTRACT

A surface active agent comprising an arylated methyl ester of a fatty acid, or mixture of fatty acids, derived from biodiesel or a triglyceride source is disclosed. The fatty acid mixture is condensed to methyl esters and alkylated with aromatic substituents under Friedel-Crafts conditions. The alkylated methyl esters may be alkoxylated using a catalyst derived from fatty acids, alkaline earth salts, and strong acids. The resulting nonionic surfactant may also be sulfonated to produce one class of anionic surfactants. The alkylated methyl esters may also be directly sulfonated to produce another class of anionic surfactants.

4 Claims, No Drawings

SURFACE ACTIVE AGENTS DERIVED FROM BIODIESEL-BASED ALKYLATED AROMATIC COMPOUNDS

CROSS-REFERENCE TO RELATED APPLICATIONS

This application is the National Phase of International Application PCT/US2011/052085, filed Sep. 19, 2011, which designated the U.S. and which claims priority to U.S. application Ser. No. 61/388,224 filed Sep. 30, 2010. The noted applications are incorporated herein by reference.

FIELD

Embodiments of the present invention generally relate to surface active agents and processes of making them. More specifically, embodiments described herein relate to surfactants derived from natural or renewable sources.

BACKGROUND

Surfactants are widely used to make detergents. Surfactants for detergents generally have a hydrophobic component and a hydrophilic component. The hydrophobic component generally attracts an otherwise water-insoluble material, and the hydrophilic component allows that material to be dispersed in water. The hydrophobic component usually has a hydrocarbon tail for maximum affinity with oils and greases, and the hydrophilic component is usually rich in oxygen, or is ionic for affinity to water molecules.

Components for surfactants are conventionally sourced from the petrochemical industry in the form of linear alkylbenzenes, detergent alcohols, linear alpha olefins, and paraffins. As petrochemical sources rise in cost, and to offset known environmental challenges associated with petrochemical sources in general, surfactants from components sourced from renewable or natural sources are becoming attractive.

SUMMARY

Embodiments described herein provide a chemical compound that has a carboxyl group, which is a carbon atom attached to a carbonyl oxygen and a hydroxyl oxygen, a hydrocarbon chain attached to the carbon atom, a methyl-terminated polyethoxy group attached to the hydroxyl oxygen, and a sulfonated aromatic group attached to the hydrocarbon chain at a secondary location.

Other embodiments provide a precursor for making a surface active agent, the precursor formed from a methyl ester of a long-chain fatty acid alkylated with an aromatic group at a secondary location and then polyalkoxylated.

Other embodiments provide a method of making a chemical composition by forming an unsaturated fatty acid methyl ester composition by subjecting a vegetable oil or biodiesel precursor to an esterification process, forming an aromatic alkylate from the unsaturated fatty acid methyl ester composition by performing an aromatic alkylation process on the unsaturated fatty acid methyl ester composition, and ethoxylating the aromatic alkylate

DETAILED DESCRIPTION

Surprisingly useful surface active agents have the general formula

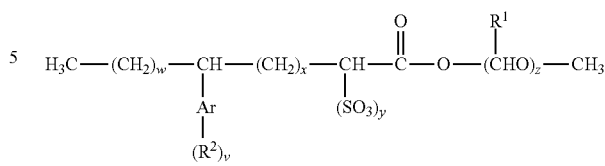

where each $R^1$ is independently hydrogen, a methyl group, or an ethyl group, and $R^2$ is hydrogen, methyl, ethyl, propyl, butyl, or a sulfonate $(SO_3)$ group, wherein y may be 0 or 1 and v may be 0, 1, or 2. Ar is an aromatic substituent, which may be a single benzene-type ring or a polynuclear aromatic core having two or three fused benzene-type rings. The aromatic substituent may be substituted, as indicated by the $R^2$ group. Thus, the entire aromatic substituent may be phenyl, toluoyl, xylyl, or a substituted naphtyl or anthracyl group.

The surface active agents described herein can be readily made from natural or renewable sources of unsaturated fatty acids. Chemical compounds available by the methods described herein have a carboxyl group with a hydrocarbon chain attached to the carbon atom and an aromatic group attached to the hydrocarbon chain at a secondary location. A methyl group, or a polyalkoxy chain, for example a polyethoxy chain, terminated by a methyl group, is attached to the hydroxyl oxygen of the carboxyl group. The aromatic group, or the first carbon atom of the hydrocarbon chain counting from the carbonyl carbon atom, or both, may additionally be sulfonated in some embodiments.

An unsaturated fatty acid methyl ester having the general formula

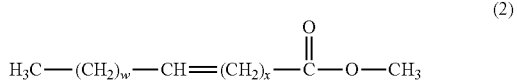

is condensed from the fatty acid and methanol and then alkylated with an aromatic group, e.g. arylated, to produce an arylate having the general formula

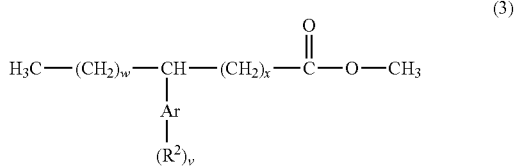

wherein $R^2$ is hydrogen or a methyl group, and v is 0, 1, or 2. The arylate may then be polyethoxylated to produce a surface active agent having the general formula

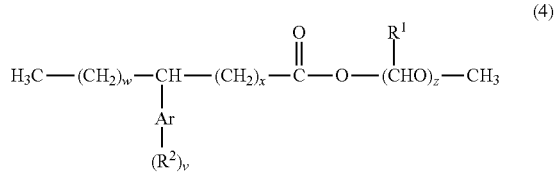

or sulfonated to produce a surface active agent having the general formula

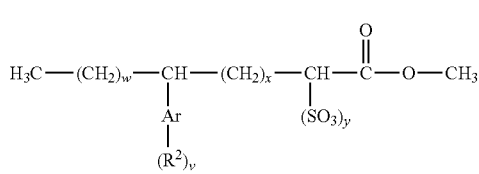

(5)

wherein $R^2$ may additionally be a sulfonate group and y is 0 or 1. The polyethoxylated aromatic alkylate (4) may also be sulfonated to produce the full arylated fatty acid methyl ester ethoxylate sulfonate. If the surface active agent is sulfonated at any location, or if $R^2$ is an $SO_3$ group in structure (1), the surface active agent is an anionic surfactant. Otherwise, the surface active agent is nonionic. It should be noted that sulfonation may produce a distribution of molecules having one or more sulfonate groups, in addition to unsulfonated molecules. The carbon atom immediately adjacent to the carbonyl carbon atom may be sulfonated, and one or more of the aromatic carbon atoms may be sulfonated. Depending on the aromatic species, sulfonation may yield a distribution of molecules having from one to five sulfonate groups.

Unsaturated fatty acids suitable for practicing the methods disclosed herein may be obtained from any triglyceride source, such as yellow grease, tallow, lard, vegetable oils, fish oils, algae oils, or biodiesel sources. Biodiesel varieties such as B-100 biodiesel derived from either palm oil or canola oil are generally suitable. Additionally, saturated fatty acids, triglycerides, and fatty acid methyl esters may be dehydrogenated using a conventional dehydrogenation catalyst to produce unsaturated fatty acids. A mixture of unsaturated fatty acids may be converted to mixed methyl esters by condensation with methanol to form unsaturated mixed methyl esters. The unsaturated mixed methyl esters may be alkylated or arylated at the site of one or more of the carbon-carbon double bonds under Friedel-Crafts reaction conditions in the presence of an aromatic component such as benzene or toluene to form an aromatic alkylate.

In some embodiments, a biodiesel source may be preprocessed by distillation or dehydrogenation to remove nonreactive saturates, or to convert them into reactive unsaturates. Polyunsaturated species may also be used, alone or mixed with monounsaturates, to form surface active agents according to the processes described herein. Polyunsaturates will generally form dark-colored agents that will be more useful in applications with low sensitivity to color, such as enhanced oil recovery applications. Polyunsaturates may also be partially hydrogenated to produce monounsaturates. The lightly colored or white agents derived from monounsaturates are generally preferred for consumer detergent applications.

Canola oil, for example, typically contains about 7% saturates, about 30% polyunsaturates, with the balance monounsaturates. The proportions of saturates, monounsaturates, and polyunsaturates may be adjusted, as described above, with any desired combination of hydrogenation, dehydrogenation, and distillation to produce a desired biodiesel-derived feedstock.

The aromatic alkylate may be alkoxylated at the hydroxyloxygen of the ester by adding an alkylene oxide, for example ethylene oxide or propylene oxide, or a mixed alkylene oxide, in the presence of a catalyst derived from a fatty acid, an alkaline earth salt, and a strong acid, which may further be derived from a glycol. Suitable catalysts for such reactions are described in commonly assigned U.S. Pat. No. 7,629,487.

An unsaturated fatty acid methyl ester material was prepared using B100 biodiesel derived from palm oil or canola oil. The natural fatty acids were condensed with methanol under basic conditions, and the resulting methyl esters were reacted with benzene using HF as a catalyst. The resulting arylated methylester was distilled to recover and isolate the mono-arylated methyl ester. A nonionic surfactant was then prepared by reacting the mono-arylated mixture with ethylene oxide under an inert atmosphere at 180° C. using a catalyst described above. Reaction pressure is maintained below about 60 psig by adjusting the rate of addition of ethylene oxide. The reaction was then digested and cooled, and the catalyst neutralized with acetic acid to form the nonionic surfactant. The resulting material was water soluble and had surfactant properties. An anionic surfactant was then prepared from the nonionic surfactant by reacting with chlorosulfonic acid or with a mixture of air and $SO_3$ to form the anionic surfactant. The resulting material was water soluble and had surfactant properties.

Canola oil was condensed into methyl esters, arylated, and distilled to recover monoarylates from the resulting product. The resulting monoarylate mixture, primarily octadecanoic acid, 9 or 10-phenyl, methyl ester, when ethoxylated as described above, was diluted in water, 8 grams of sample in 792 grams of water, to produce an 800 gram mixture. The mixture displayed a pH of 5.1, an equilibrium surface tension of 35.66 mN/m, and interfacial tension with mineral oil of 8.74 mN/m. Table 1 lists the above results along with some comparative samples.

TABLE 1

Comparison of an Arylated Methyl Ester Ethoxylate with Various Surfactants

| | Sample | | | | |
|---|---|---|---|---|---|
| | 1 | 2 | 3 | 4 | 5 |
| Grams Sample | 8 | 8 | 8 | 8 | 8 |
| Grams Water | 792 | 792 | 792 | 792 | 792 |
| pH | 4.9 | 5.1 | 5.3 | 5.4 | 5.1 |
| Surface Tension, mN/m | 28.5 | 31.5 | 35.5 | 35.2 | 35.7 |
| Interface Tension (mineral oil), mN/m | 2.48 | 0.95 | 2.09 | 3.35 | 8.74 |

Sample 1 = linear alcohol ethoxylate surfactant (Huntsman SURFONIC ® L24-7)
Sample 2 = nonylphenol ethoxylate surfactant (Huntsman SURFONIC N-95)
Samples 3 and 4 = fatty acid methyl ester ethoxylates (Huntsman SURFONIC ME-400 and ME-530)
Sample 5 = 9/10-phenyl-octadecanoic acid, methyl ester The arylated methyl ester described above was sulfonated by exposure to air and $SO_3$, and the resulting product diluted in water. Table 2 shows properties of the resulting mixtures.

TABLE 2

Comparison of Sulfonated Arylated Methyl Ester Ethoxylates with a Known Surfactant

| | Sample | | |
|---|---|---|---|
| | 1 | 2 | 3 |
| Grams Sample | 10 | 10 | 10 |
| Grams Water | 990 | 990 | 990 |
| pH | 5.9 | 5.7 | 5 |
| Surface Tension, mN/m | 37.5 | 32.1 | 34.9 |
| Interface Tension (mineral oil), mN/m | 6.2 | 5.3 | 5.0 |

Sample 1 = Arylated methyl ester sulfonate #1
Sample 2 = Arylated methyl ester sulfonate #2
Sample 3 = Huntsman A-215 linear alkyl benzene sulfonate, sodium salt prepared by air/SO3 sulfonation of A-215 alkyl benzene.

By practicing the methods described herein, a new class of useful surfactants may be made from biodiesel and/or other natural fatty acid sources.

While the foregoing is directed to embodiments of the present invention, other and further embodiments of the invention may be devised without departing from the basic scope thereof, and the scope thereof is determined by the claims that follow.

The invention claimed is:

1. A chemical compound, comprising:
   a carboxyl group comprising a first carbon atom bonded to a carbonyl oxygen and a hydroxyloxygen, wherein a methyl group or a methyl-terminated polyethoxy group is bonded to the hydroxyl oxygen of the carboxyl group;
   a hydrocarbon chain bonded to the first carbon atom; and
   an aromatic group bonded to the hydrocarbon chain at a secondary location.

2. The compound of claim 1, wherein a methyl-terminated polyethoxy group is bonded to the hydroxyl oxygen and wherein a sulfonate group is bonded to the aromatic group.

3. The compound of claim 1, wherein the hydrocarbon chain and the carboxyl group are derived from a vegetable source.

4. A chemical composition comprising a compound as recited in claim 1.

* * * * *